United States Patent

Hüglin et al.

[11] Patent Number: 5,929,270
[45] Date of Patent: Jul. 27, 1999

[54] PROCESS FOR PREPARING DISTYRYLBIPHENYL COMPOUNDS

[75] Inventors: Dietmar Hüglin, Eimeldingen; Robert Hochberg, Freiburg; Oliver Becherer, Schwörstadt; Reinhard Weigmann, Kandern, all of Germany

[73] Assignee: Ciba Specialty Chemicals Corporation, Tarrytown, N.Y.

[21] Appl. No.: 09/081,426

[22] Filed: May 19, 1998

[51] Int. Cl.⁶ .......... C07C 255/00; C07C 61/29; C07G 1/00
[52] U.S. Cl. .............. 558/413; 562/58; 562/73; 562/83; 562/88; 562/30
[58] Field of Search ................... 562/58, 73, 83, 562/88, 30; 558/413

[56] References Cited

U.S. PATENT DOCUMENTS

| | | | |
|---|---|---|---|
| 2,657,228 | 10/1953 | Häusermann et al. | 260/456 |
| 4,147,648 | 4/1979 | Gunter et al. | 562/73 |
| 4,424,170 | 1/1984 | Weber | 260/505 |
| 5,145,991 | 9/1992 | Weber et al. | 562/87 |
| 5,177,255 | 1/1993 | Bader et al. | 562/87 |
| 5,332,861 | 7/1994 | Guglielmetti | 562/87 |

OTHER PUBLICATIONS

J. Org. Chem. USSR, 16, (1980), pp. 342–347.

*Primary Examiner*—Johann Richter
*Assistant Examiner*—Joseph Murray
*Attorney, Agent, or Firm*—Kevin T. Mansfield

[57] ABSTRACT

A process is provided for the production of compounds having the formula:

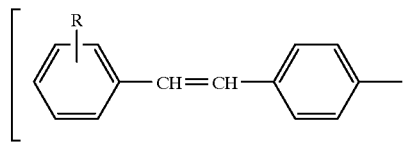

(1)

-continued

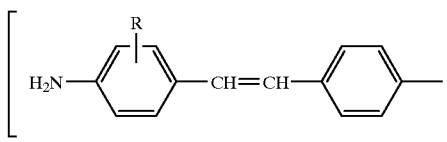

in which R is hydrogen, $C_1$–$C_5$alkyl, cyano or halogen; M is hydrogen or a salt-forming colorless cation; and n is 2;

which process comprises reductively de-aminating a compound having the formula:

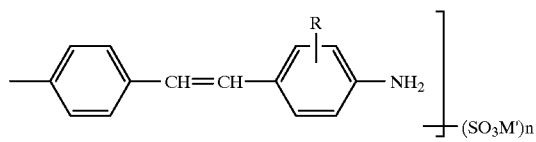

(2)

in which R and n have their previous significance and M' is hydrogen, a salt-forming colorless cation or optionally substituted phenyl; and converting any optionally substituted phenyl group M' to a group M.

The present invention also provides processes for the production of the compounds of formula (2) and various novel intermediates for use in the new processes.

The compounds of formula (1) are useful as fluorescent whitening agents.

32 Claims, No Drawings

PROCESS FOR PREPARING DISTYRYLBIPHENYL COMPOUNDS

The present invention relates to a new process for preparing distyrylbiphenyl compounds and to new intermediate compounds for use in the new process.

Distyrylbiphenyl compounds are an important class of fluorescent whitening agents for use in the fluorescent whitening of a wide range of substrates such as textiles, in particular cotton, polyamide and wool, or for the fluorescent whitening of paper. The distyrylbiphenyl compounds may be applied to the substrate, e.g., via a detergent, an application liquid or a coating composition.

The object of the present invention is to provide a new process for the preparation of distyrylbiphenyl compounds.

According to a first aspect of the present invention, there is provided a process for the production of compounds having the formula:

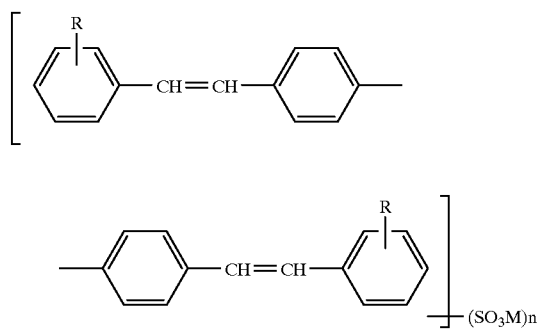

(1)

in which R is hydrogen, $C_1$–$C_5$alkyl, cyano or halogen; M is hydrogen or a salt-forming colourless cation; and n is 2;

which process comprises reductively de-aminating a compound having the formula:

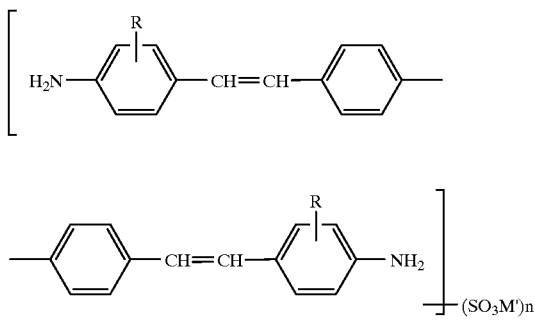

(2)

in which R and n have their previous significance and M' is hydrogen, a salt-forming colourless cation or optionally substituted phenyl; and converting any optionally substituted phenyl group M' to a group M.

Examples of radicals R are hydrogen, methyl, ethyl, propyl, butyl, pentyl, cyano, chlorine and bromine; hydrogen, methyl, ethyl, cyano and chlorine being preferred.

Examples of cations M or M' include alkali metal cations, such as sodium and potassium, ammonium cations such as ammonium, mono-, di-, tri- or tetra-$C_1$–$C_4$-alkylammonium, mono-, di- or tri-$C_1$–$C_4$-hydroxyalkylammonium or ammonium that is di- or tri-substituted with a mixture of $C_1$–$C_4$-alkyl and $C_1$–$C_4$-hydroxyalkyl groups. When M' is optionally substituted phenyl, examples include halo-phenyl, preferably p-chlorophenyl, $C_1$–$C_4$alkyl-phenyl, especially p-methylphenyl or $C_1$–$C_4$alkoxy-phenyl, but unsubstituted phenyl is particularly preferred.

Preferred compounds of formula (2) are those having the formula:

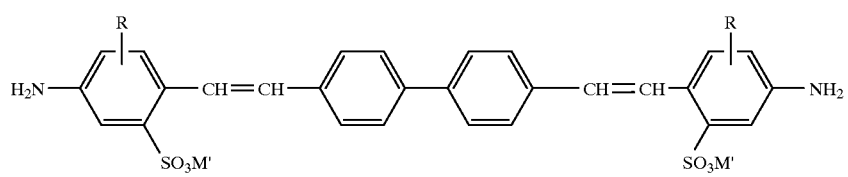

(3)

in which R has its previous significance and is preferably hydrogen, and M' has its previous significance and is preferably hydrogen, sodium or phenyl.

The reductive de-amination process according to the present invention may be conducted, for example, by directly replacing the amino groups with hydrogen, by reacting the compound of formula (2) with hydroxylamino-O-sulfonic acid under alkaline conditions or with an aqueous solution of chloramine, in the manner described in JACS 100 (1978), 341.

It is preferred, however, to conduct the de-amination process according to the present invention by firstly converting the compound of formula (2) into the corresponding diazo compound having the formula:

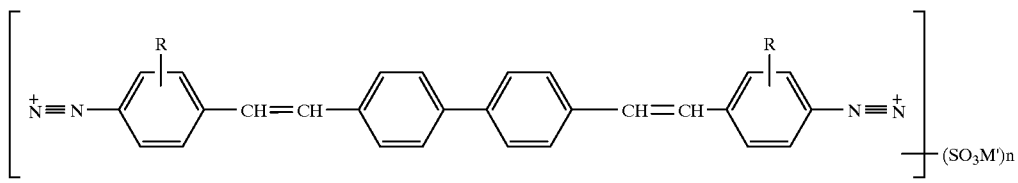

(4)

in which R, M' and n have their previous significance and M' is hydrogen, a salt-forming colourless cation or optionally substituted phenyl; and separately or, preferably, simultaneously, reductively cleaving the respective diazo groups. Subsequently, any optionally substituted phenyl group M' may be converted to a group M.

The diazotisation may be conducted by any conventional process.

The reduction may be effected using ethanol and CuO (Helv. 9 (1926) 929; ethanol and Zn (Bull. Soc. Chim. Fr. 1950, 466; hypophosphorous acid (Synthesis 1991, 469 & JACS 76 (54) 290; formic acid (Bull. Soc. Chim. Fr. 1950, 466); formaldehyde/KOH (JACS 61 (1939) 2418; or Fe in dimethylformamide (J.Org.Chem.1995, 60, 1713–1719.

Other reducing agents are described in Houben-Weyl X/3, 115–144 and V 2b, 309–314 and further suitable solvents include methanol, benzyl alcohol, 1,4-dioxan, tetrahydrofuran, 1,2-dimethoxyethane, 1,3-dioxolan and dimethylformamide.

When, in the compounds of formula (4), R is cyano or halogen, the respective diazo groups may be conveniently reductively cleaved in the presence of copper and cyano- or halo ions, under Sandmeyer reaction conditions.

When, in the compounds of formula (4), M' is hydrogen or a salt-forming colourless cation, the reductive cleavage of the diazo groups according to the preferred de-amination process of the present invention is preferably effected in an alcohol solvent, preferably a $C_1$–$C_4$ alcohol, especially ethanol, or benzyl alcohol. The reaction is preferably conducted in the presence of a catalyst, especially copper, zinc, UV light or, in particular, copper (I)-oxide.

On the other hand, when, in the compounds of formula (4), M' is optionally substituted phenyl, the reductive cleavage of the diazo groups according to the preferred de-amination process of the present invention is preferably effected in hypophosphorous acid.

Any optionally substituted phenyl group M' may be converted to a group M by known methods such as the use of an alkaline material, e.g. potassium carbonate in a suitable solvent such as ethylcellosolve.

Preferred intermediates of formula (4) are those having the formula:

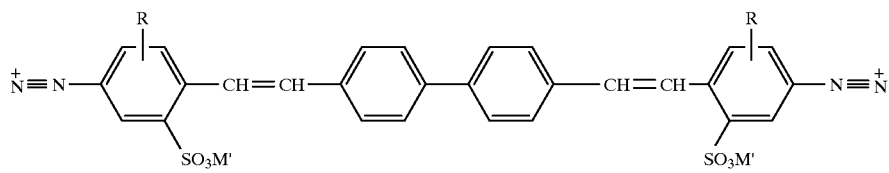

(5)

in which R has its previous significance and is preferably hydrogen, cyano or chloro, and M' has its previous significance and is preferably hydrogen, sodium or phenyl.

The compounds of formula (2), (3), (4) and (5) are new compounds and, as such, form a second aspect of the present invention. In addition to their use as a reactant in the process according to the first aspect of the present invention, the compounds of formula (4) and (5) may also also find use, e.g., as dyestuff intermediates.

The process according to the first aspect of the present invention provides, in particular, the following compounds of formula (1):

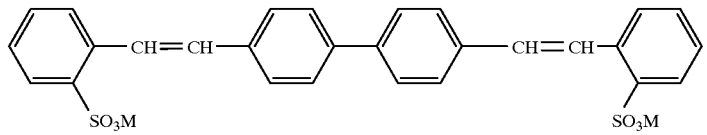

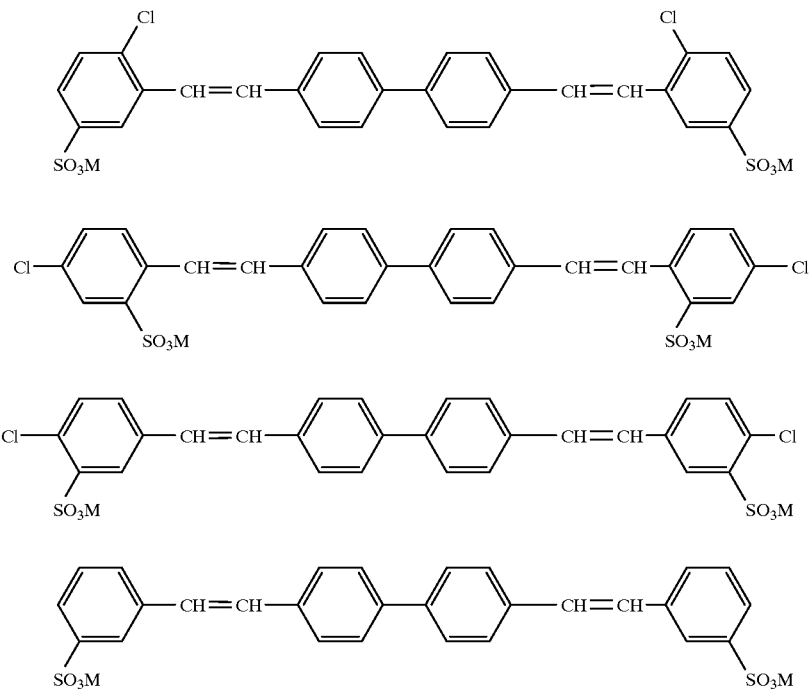

According to a third aspect of the present invention, there is provided a process for the production of a compound having the formula (2) comprising reducing a compound having the formula:

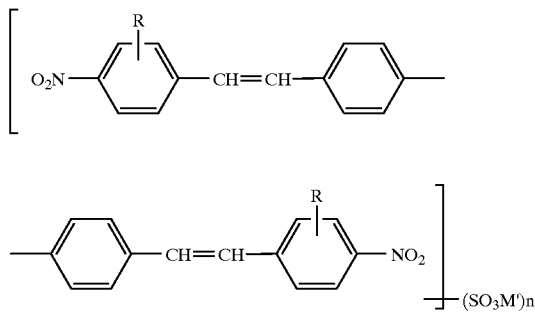

(6)

in which R, M' and n have their previous significance.

The reduction of the compound of formula (6) may be effected by methods known per se, but the chosen method may vary depending on the nature of M'. For example, when, in the compounds of formula (6), M' is hydrogen or a salt-forming colourless cation, the reduction is preferably effected using iron and acetic acid or $SnCl_2$ in HCl.

On the other hand, when, in the compounds of formula (4), M' is optionally substituted phenyl, the reduction is preferably conducted using iron in cyclohexanone. Other possible reduction systems, for both process variants, include other metal catalysts such as zinc or tin in hydrochloric acid, the use of catalytic hydrogenation or the use of hydrazine as reducing agent.

The compounds of formula (6) are new and, as such, form a further, fourth aspect of the present invention.

Preferred compounds of formula (6) are those having the formula:

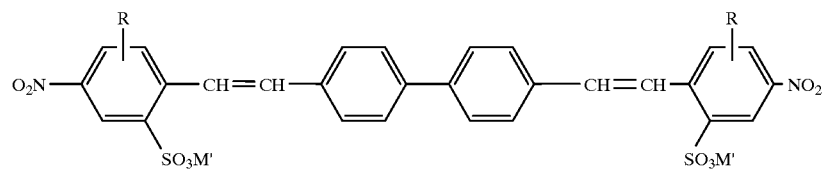

(7)

in which R has its previous significance and is preferably hydrogen, and M' has its previous significance and is preferably hydrogen, sodium or phenyl.

According to a fifth aspect of the present invention, there is provided a process for the production of a compound of formula (6) comprising reacting one mole of a compound having the formula:

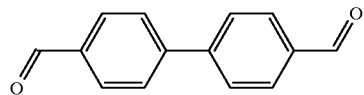
(8)

with two moles of a compound having the formula:

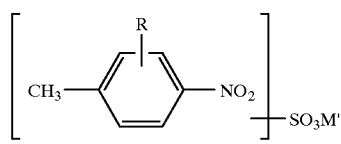
(9)

in which R and M' have their previous significance.

The compounds of formula (8) and (9) are known compounds and may be produced by methods known per se.

Preferred compounds of formula (9) are those having the formula:

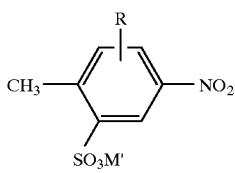
(10)

in which R has its previous significance and is preferably hydrogen, and M' has its previous significance and is preferably hydrogen, sodium or phenyl.

The process according to the fifth aspect of the present invention is a conventional base-catalyzed Knoevenagel condensation, the general reaction scheme for which is described, e.g., in K. D. Becker, synthesis 1983, 341–368. Again, the selected condensation conditions will vary depending on the nature of M'. For example, when, in the compounds of formula (9), M' is hydrogen or a salt-forming colourless cation, the condensation reaction is preferably effected using dimethylsulfoxide as solvent and pyrrolidine as base.

On the other hand, when, in the compounds of formula (9), M' is optionally substituted phenyl, the condensation reaction is preferably conducted using ethylcellosolve as solvent and piperidine as base. Other solvents which can be used include dimethyl formamide and toluene, and an alternative base is pyrrolidine.

The reaction is conveniently effected at an elevated temperature, e.g., a temperature in the range of from 100 to 200° C., preferably in the range of from 130 to 180° C. If desired, any phenyl group M' may be saponified to a hydrogen or sodium group M'.

The present invention also provides, as a sixth aspect, a straight-through process for the production of compounds having the formula:

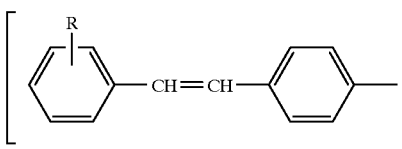

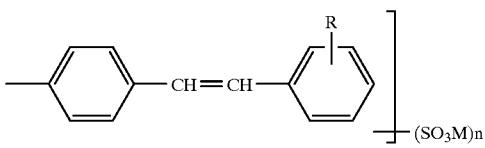
(1)

in which R is hydrogen, $C_1$–$C_5$alkyl or halogen; M is hydrogen or a salt-forming colourless cation; and n is 2;

which process comprises:

A) reacting one mole of a compound having the formula:

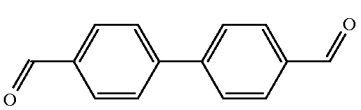
(8)

with two moles of a compound having the formula:

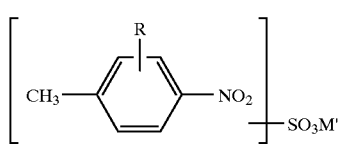
(9)

in which R and M' have their previous significance, to produce a compound having the formula:

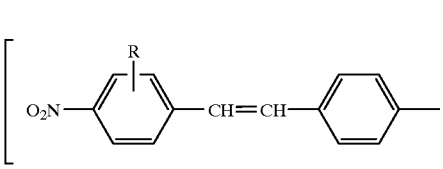

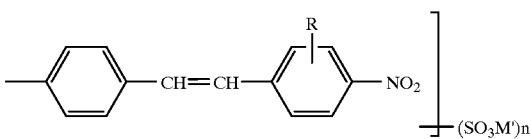
(6)

in which R, M' and n have their previous significance;

B) reducing the compound of formula (6) obtained in step (A) to produce a compound of formula:

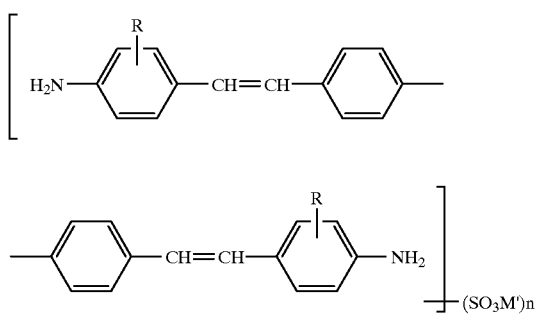

(2)

in which R, M' and n have their previous significance; and

C) reductively de-aminating the compound of formula (2), preferably by firstly diazotising the compound of formula (2) obtained in step (B) to produce a compound having the formula:

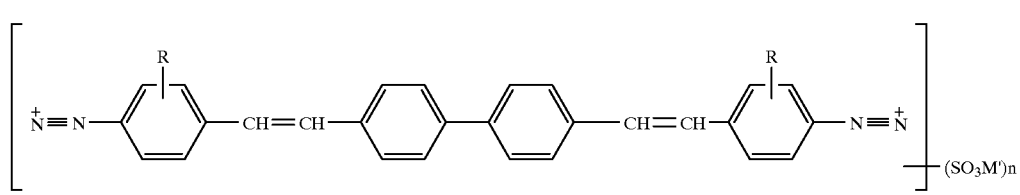

(4)

in which R, M' and n have their previous significance and then reducing the compound of formula (4) so obtained to obtain a compound of formula (1).

As already indicated, the distyrylbiphenyl compounds of formula (1), obtained according to the present invention, are useful for the fluorescent whitening of a wide range of substrates such as textiles and paper and they may be applied to the substrate via a detergent, an application liquid or a coating composition. For this purpose, they are usually diluted to the optimum concentration for the particular application by the addition of further auxiliaries, or water.

The diluted compositions so obtained may also contain customary formulation aids such as dispersants, builders, protective colloids, stabilizers, preservatives, perfumes, pigments, enzymes and sequestering agents.

The dispersants used are preferably nonionic such as fatty alcohols, ethoxylation products of fatty alcohols or fatty acids; or anionic such as condensation products of aromatic sulfonic acids with formaldehyde, e.g. those based on sulfonic acids of ditolyl ether or on naphthalene sulfonates, or those based on lignin sulfonates.

Examples of builders or protective colloids are modified polysaccharides derived from cellulose or heteropolysaccharides, such as xanthan or carboxymethyl cellulose; or aluminium silicates or magnesium silicates.

Examples of further auxiliaries which may be added, as stabilizers, are ethylene glycol, propylene glycol as well as further dispersants.

Examples of preservatives include 1,2-benzisothiazolin-3-one, formaldehyde and chloracetamide.

The following Examples further illustrate the present invention.

EXAMPLE 1

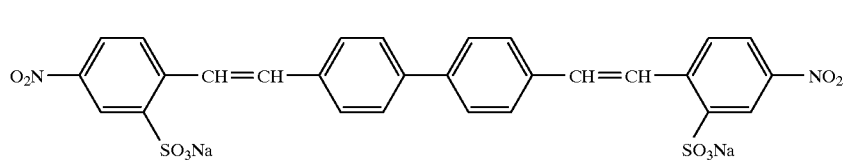

(101)

256 g of the sodium salt of 4-nitrotoluene-2-sulfonic acid and 110 g of biphenyl-4,4'-dialdehyde are dispersed in 600 ml of dimethyl sulfoxide, treated with 20 g of pyrrolidine under nitrogen and stirred for 4 hours at 93–94° C. After the addition of a further 20 g of pyrrolidine, the mixture is stirred for a further 4 hours at 93–94° C. A further 10 mg of pyrrolidine is then added and the mixture is stirred for a further 4 hours at 105° C. After allowing the reaction mixture to cool, 1000 mls of isopropanol are run into the reaction mixture at 25° C., the mixture is stirred for 1 hour and filtered. The orange precipitate is washed with 600 mls of isopropanol and dried in vacuum at 60° C. The dry orange powder so obtained is dissolved in deionised water at 90° C., cooled to 50° C., salted out by the addition of 280 g of sodium chloride and washed with a 10% aqueous sodium chloride solution. After filtering off and drying in vacuum at 60° C., 275 g of the compound of formula (101), as an orange powder, are obtained.

$^1$H-NMR (MeOD): δ (in ppm)=8.73 (d, 2H, aromatic), 8.18 (dd, 2H, aromatic), 8.13 (2H, —CH=CH—), 8.00 (d, 2H, aromatic), 7.68 (d, 4H, aromatic), 7.63 (d, 4H, aromatic), 7.37 (d, 2H, —CH=CH—).

EXAMPLE 2

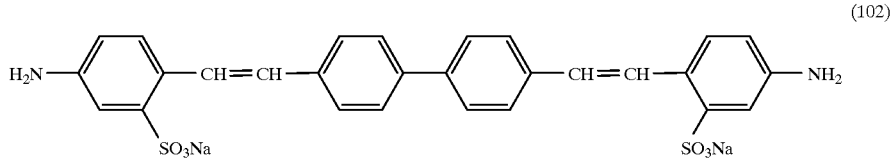

(102)

160 g of iron turnings are dispersed in 700 mls of deionised water, treated with 7 g of acetic acid and 10 g of sodium acetate and stirred for 30 minutes at 99° C. There is then added to this mixture, portionwise, a suspension of 256 g of the compound of formula (101) obtained in Example 1 and 2 g of acetic acid, in 1000 mls of deionised water. After half of the suspension has been added over 90 minutes, the mixture is stirred for 60 minutes at 95° C., before the rest of the suspension is added over 180 minutes. After the addition of a further 40 g of iron, the reaction mixture is stirred for a further 1 hour at 100° C. The pH of the reaction mixture is adjusted to 9.2–9.4 with 15% aqueous sodium carbonate solution and the reaction mixture is filtered hot. The filter residue is heated to 95° C. in 3000 mls of deionised water at pH 10, filtered through a hot pressure suction filter and washed with 500 mls of hot water. The combined filtrates are filtered after cooling and provide 170 g of a compound having the formula (102), as a yellow powder.

$^1$H-NMR (DMSO-$d_6$):δ (in ppm)=5.93 (d, 2H, —CH=CH—), 5.57 (d, 4H, aromatic), 5.51 (d, 2H, aromatic), 5.48 (d, 4H, aromatic), 5.12 (d, 2H, aromatic), 4.84 (d, 2H, —CH=CH—), 4.70 (dd, 2H, aromatic).

EXAMPLE 3

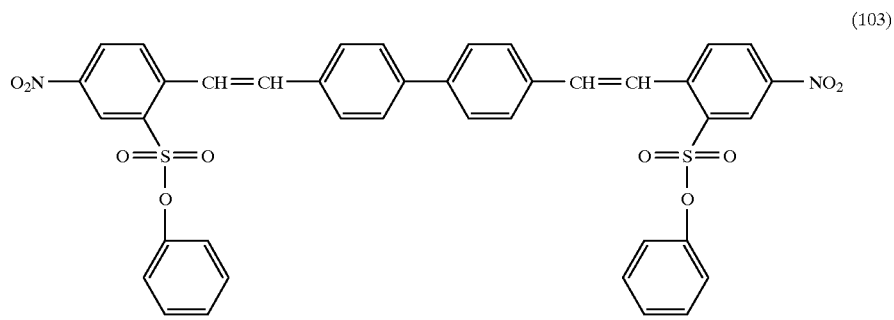

(103)

148 g 4-nitrotoluene-2-sulfonic acid phenyl ester and 50 g of biphenyl-4,4'-dialdehyde are heated to 100° C. in 400 mls of ethylcellosolve under nitrogen. There are added to this mixture 19 g of piperidine and 12 g of ethylene glycol and the whole mixture is heated for 14 hours at 135° C. After cooling, the mixture is filtered, the precipitate is washed with a little ethanol and dried in vacuum at 70° C. The orange powder so obtained is boiled in 600 mls of acetone and the mixture is filtered hot. After cooling, the precipitate is filtered off and dried in vacuum at 60° C. There are obtained 140 g of a compound having the formula (103), as an orange powder.

Elemental analysis of the compound having the formula (103) and having the empirical formula $C_{40}H_{28}N_2S_2O_{10}$ gives:

Req. % C 63.15; H 3.71; N 3.68; S 8.43; O 21.03. Found % C 63.01; H 3.77; N 3.80; S 8.21; O 21.10.

EXAMPLE 4

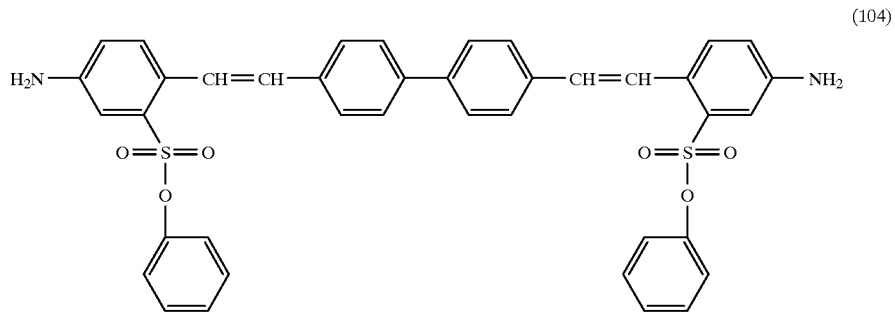

(104)

90 g of iron turnings are dispersed in 600 mls of deionised water, treated with 6 g of acetic acid and heated to 99° C. After the addition of 600 mls of hot cyclohexanone, there are then added to this mixture, portionwise, over 2 hours, 140 g of the compound of formula (103) obtained in Example 3. A further 90 g of iron, 6 g of acetic acid and 4 g of sodium acetate are added to the reaction mixture which is stirred for a further 2 hours at 98° C. After the addition of 30 g of sodium carbonate, the reaction mixture is filtered hot and washed with 200 mls of cyclohexanone and 500 mls of water. The organic phase of the filtrate is separated and the aqueous phase, after the addition of 250 g of sodium chloride, is extracted with cyclohexanone. The combined organic phases are steam distilled, the residue is filtered and dried in vacuum at 70–80° C. to provide 127.8 g of a compound having the formula (104), as an orange powder.

$^1$H-NMR (acetone-$d_6$):δ (in ppm)=8.01 (d, 2H, —CH═CH—), 7.85 (d, 2H, aromatic), 7.75 (d, 4H, aromatic), 7.65 (d, 4H, aromatic), 7.35 (t, 4H, aromatic), 7.27 (t, 2H, aromatic), 7.21 (d, 2H, —CH═CH—), 7.16 (d, 2H, aromatic), 7.09 (d, 2H, aromatic), 7.03 (dd, 2H, aromatic).

25 g of the compound of formula (104) obtained in Example 4 are dissolved in 250 mls of hot acetone and the solution obtained is added to 150 g of acetic acid (80%). the acetone is removed using a rotary evaporator, the residue is treated with 25 g hydrochloric acid (32%) and cooled to 5° C. There are then added to this acidified residue, over 45 minutes at 5–8° C., 12 mls of aqueous sodium nitrite solution (46%). The resulting red solution is stired for 4 hours at 8° C. and then treated with 100 mls of hypophosphorous acid (50%). When no further nitrogen is liberated, the mixture is diluted with 500 mls of deionised water and washed with 500 mls of water. After drying in vacuum, there are obtained 24.9 g of a pale yellow substance. This crude product is heated to reflux in 700 mls of toluene and purified using fuller's earth and active charcoal. In this way, there is obtained a clear light orange solution which, after removing the solvent and drying in vacuum, provides 9.5 g of an orange powder having the formula (105).

$^1$H-NMR (DMSO-$d_6$):δ (in ppm)=8.20 (d, 2H, aromatic), 7.96 (d, 2H, —CH═CH—), 7.90–7.82 (m, 8H, aromatic), 7.74 (d, 4H, aromatic), 7.58 (d, 2H, —CH═CH—), 7.52 (t, 2H, aromatic), 7.40 (t, 4H, aromatic), 7.31 (t, 2H, aromatic), 7.06 (d, 4H, aromatic).

EXAMPLE 5

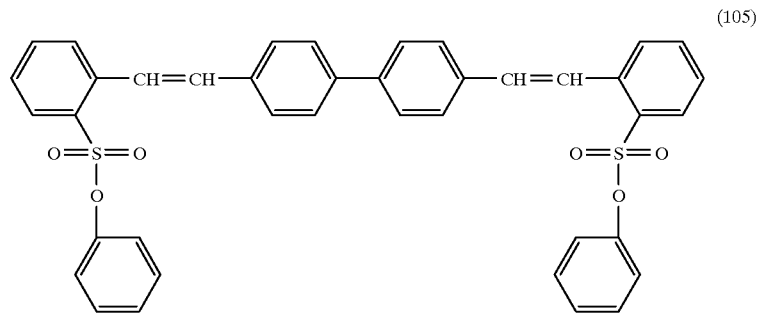

(105)

EXAMPLE 6

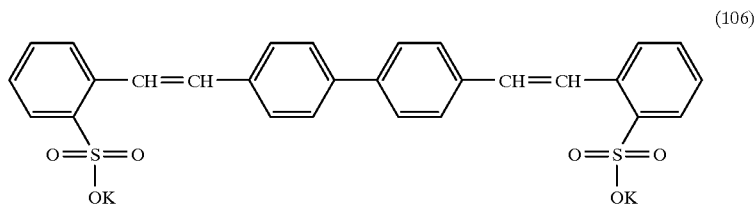
(106)

8 g of the compound of formula (105) obtained in Example 5 are dispersed in 200 mls of ethylcellosolve, heated to 135° C. and treated with 2.5 g of potassium carbonate. The mixture is stirred for 2 hours at 135° C. and, after treatment with active charcoal, is concentrated to dryness on a rotary evaporator. The yellow residue is taken up in ethanol and filtered. After washing with ethanol and drying in vacuum, there are obtained 5.7 g of a yellowish powder of formula (106).

$^1$H-NMR (DMSO-d$_6$):δ (in ppm)=8.10 (d, 2H, —CH=CH—), 7.82 (d, 2H, aromatic), 7.80 (d, 2H, aromatic), 7.71 (d, 4H, aromatic), 7.65 (d, 2H, aromatic), 7.44 (t, 2H, aromatic), 7.30 (t, 2H, aromatic), 7.15 (d, 2H, —CH=CH—).

EXAMPLE 7

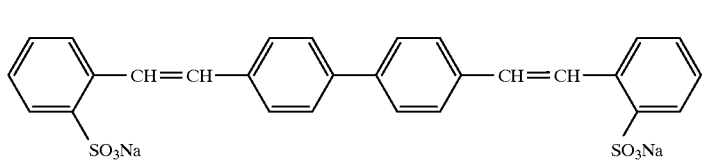
(107)

20 g of concentrated hydrochloric acid (32%) in 60 mls of deionised water are cooled to 5° C., treated with 12 mls of sodium nitrite solution (46%) and diluted to 180 mls with deionised water. To this solution there are added, dropwise, at 5–8° C. over 90 minutes, a suspension of 20 g of the compound of formula (102), produced according to Example 2, in 130 mls of deionised water. The mixture is stirred overnight and then filtered. The separated precipitate is washed with 50 mls of deionised water and then dispersed in 200 mls of ethanol. To this dispersion there are added, at 25° C., portionwise, 4 g of Cu$_2$O, whereupon, with each addition, a considerable amount of gas is evolved. The mixture so obtained is heated for 1 hour under reflux conditions, diluted with 300 mls of deionised water and adjusted to pH 8.5 using a 15% alcoholic soda solution. The solution, with the addition of active charcoal, is heated for 1 hour under reflux conditions and clarified hot over kieselguhr. After cooling, the solution is salted out by the addition of 150 g of sodium chloride, washed with 50% sodium chloride solution, filtered with suction and the filtercake is dried at 60° C. in vacuum. 12 g of the compound (107), as a yellow powder, are obtained.

$^1$H-NMR (DMSO-d$_6$):δ (in ppm)=8.20 (d, 2H, —CH=CH—), 7.85 (d, 2H, aromatic), 7.82 (d, 2H, aromatic), 7.75 (d, 4H, aromatic), 7.67 (d, 2H, aromatic), 7.42 (t, 2H, aromatic), 7.29 (t, 2H, aromatic), 7.19 (d, 2H, —CH=CH—).

We claim:

1. A process for the production of compounds having the formula:

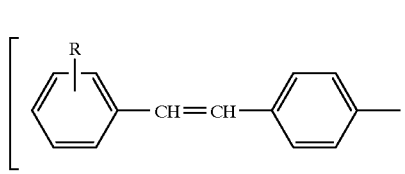
(1)

-continued

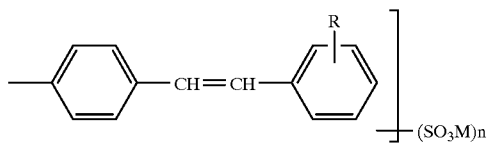

in which R is hydrogen, C$_1$–C$_5$alkyl, cyano or halogen; M is hydrogen or a salt-forming colourless cation; and n is 2;

which process comprises reductively de-aminating a compound having the formula:

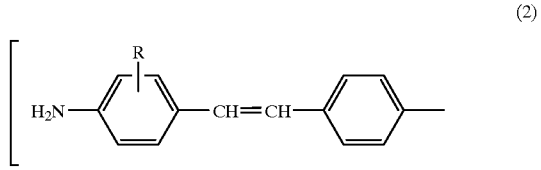
(2)

-continued

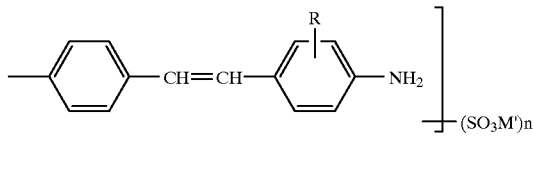

in which R and n have their previous significance and M' is hydrogen, a salt-forming colourless cation or optionally substituted phenyl; and converting any optionally substituted phenyl group M' to a group M.

2. A process according to claim 1 in which the compound of formula (2) has the formula:

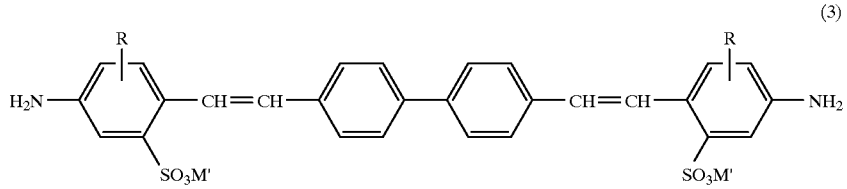

in which R and M' are a defined in claim 1.

3. A process according to claim 2 in which R is hydrogen, cyano or chloro, and M' is hydrogen, sodium or phenyl.

4. A process according to claim 1 in which firstly a compound of formula (2) is diazotised to a diazo compound having the formula:

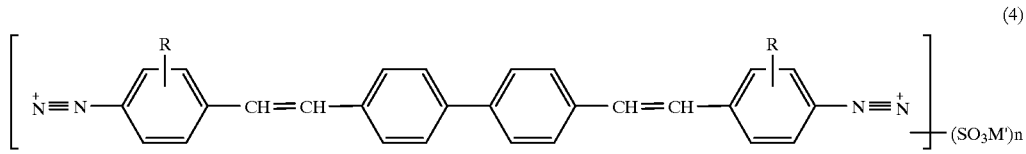

in which R, M' and n are as defined in claim 1; and then the respective diazo groups are reductively cleaved and any optionally substituted phenyl group M' is converted to a group M.

5. A process according to claim 4 in which, in the compounds of formula (4), M' is hydrogen or a salt-forming colourless cation, and the reductive cleavage of the diazo groups is effected in the presence of an alcohol or dimethylformamide, as solvent, and in the presence of copper, iron, zinc or UV light, as catalyst.

6. A process according to claim 5 in which the alcohol solvent is a $C_1$–$C_4$alcohol or benzyl alcohol.

7. A process according to claim 5 in which the reductive cleavage of the diazo groups is effected in the presence of CuO/ethanol.

8. A process according to claim 4 in which, in the compounds of formula (4), M' is optionally substituted phenyl, and the reductive cleavage of the diazo groups is effected in the presence of hypophosphorous acid.

9. A compound having the formula:

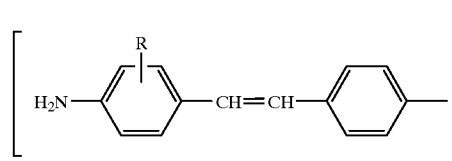

(2)

-continued

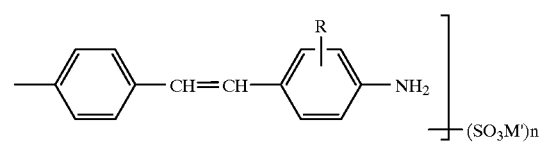

in which R is hydrogen, $C_1$–$C_5$alkyl or halogen, n is 2 and M' is hydrogen, a salt-forming colourless cation or optionally substituted phenyl.

10. A compound according to claim 9 having the formula:

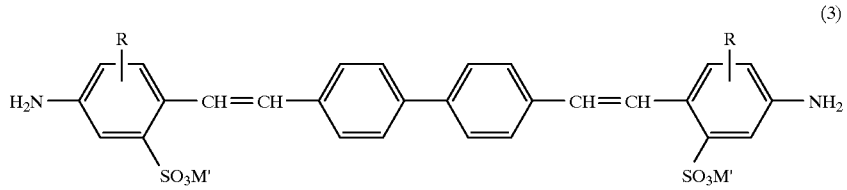

(3)

in which R and M' are as defined in claim 9.

11. A compound according to claim 10 in which R is hydrogen and M' is hydrogen, sodium or phenyl.

12. A compound having the formula:

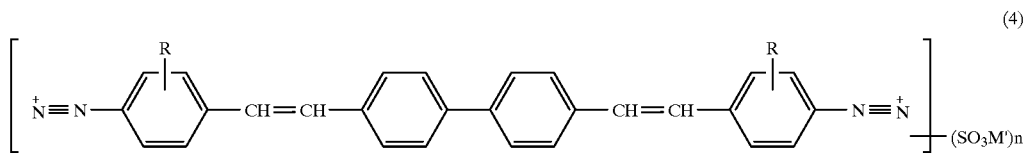

(4)

in which R, M' and n are as defined in claim 1.

13. A compound having the formula:

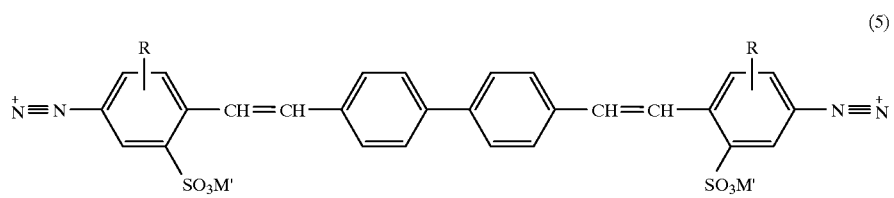

(5)

in which R and M' are as defined in claim 1.

14. A process for the production of a compound having the formula

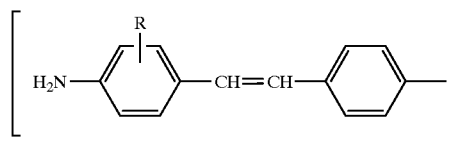

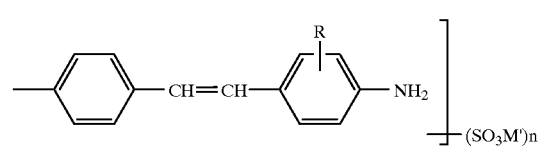

(2)

comprising reducing a compound having the formula:

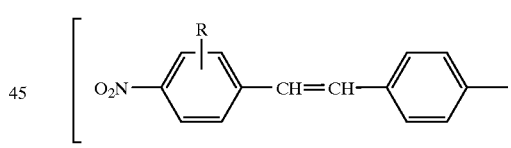

(6)

in which R, M' and n are as defined in claim 1.

15. A process according to claim 14 in which, in the compounds of formula (6), M' is hydrogen or a salt-forming colourless cation, and the reduction is effected using iron and acetic acid or $SnCl_2$ in HCl.

16. A process according to claim 14 in which, in the compounds of formula (2), M' is optionally substituted phenyl, and the reduction is conducted using iron in cyclohexanone.

17. A compound having the formula:

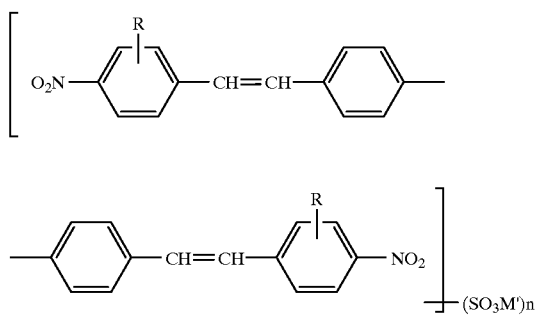
(6)

in which R, M' and n are as defined in claim 1.

18. A compound having the formula:

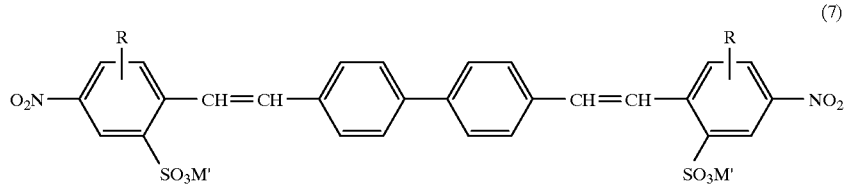
(7)

in which R and M' are as defined in claim 1.

19. A compound according to claim 18 in which R is hydrogen, and M' is hydrogen, sodium or phenyl.

20. A process for the production of a compound of formula

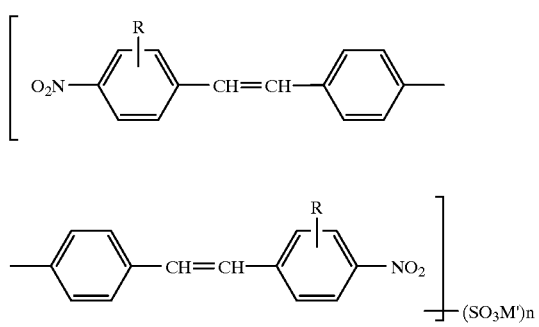
(6)

comprising reacting one mole of a compound having the formula:

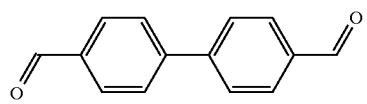
(8)

with two moles of a compound having the formula:

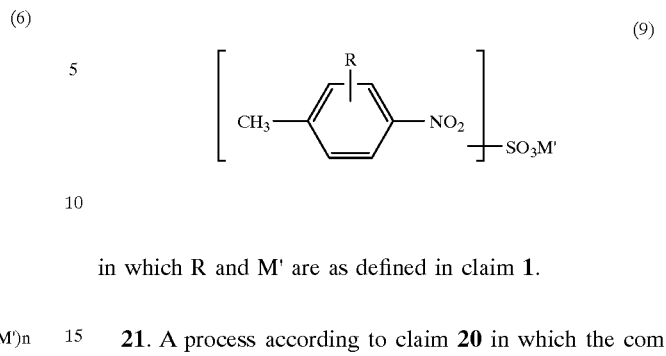
(9)

in which R and M' are as defined in claim 1.

21. A process according to claim 20 in which the compounds of formula (9) used are those having the formula:

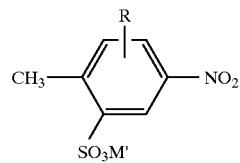
(10)

in which R is hydrogen, $C_1$–$C_5$alkyl, cyano or halogen and M' is hydrogen, a salt-forming colourless cation or optionally substituted phenyl.

22. A process according to claim 21 in which R is hydrogen and M' is hydrogen, sodium or phenyl.

23. A process according to claim 20 in which, in the compounds of formula (9), M' is hydrogen or a salt-forming colourless cation, and the condensation reaction is effected using dimethylsulfoxide as solvent and pyrrolidine as base.

24. A process according to claim 20 in which, in the compounds of formula (9), M' is optionally substituted phenyl, and the condensation reaction is conducted using ethylcellosolve as solvent and piperidine as base.

25. A process according to claim 20 in which the process is conducted at a temperature in the range of from 100 to 200° C. and in the presence of an inert solvent.

26. A process according to claim 20 in which any phenyl group M' is converted to a hydrogen or sodium group M.

27. A process for the production of compounds having the formula:

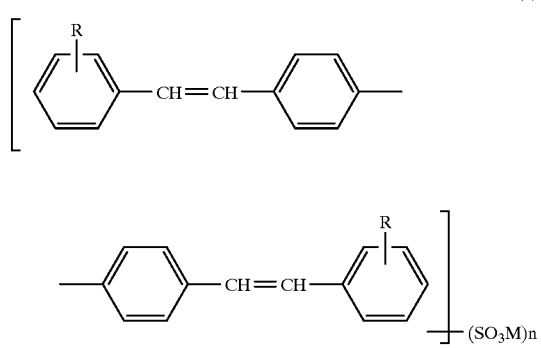

(1)

in which R is hydrogen, $C_1$–$C_5$alkyl or halogen; M is hydrogen or a salt-forming colourless cation; and n is 2;

which process comprises:

A) reacting one mole of a compound having the formula:

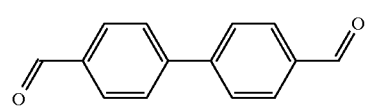

(8)

with two moles of a compound having the formula:

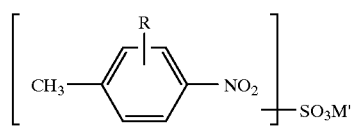

(9)

in which R and M' have their previous significance, to produce a compound having the formula

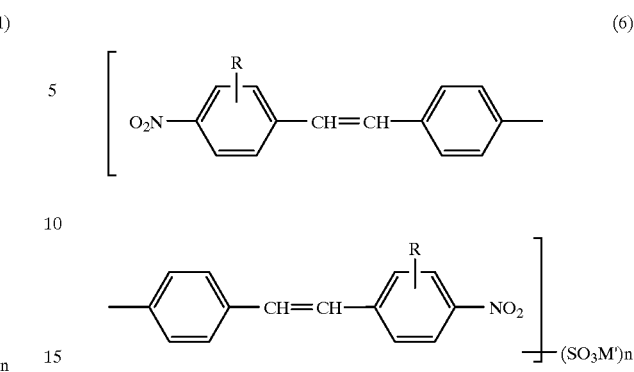

(6)

in which R, M' and n have their previous significance;

B) reducing the compound of formula (6) obtained in step (A) to produce a compound of formula:

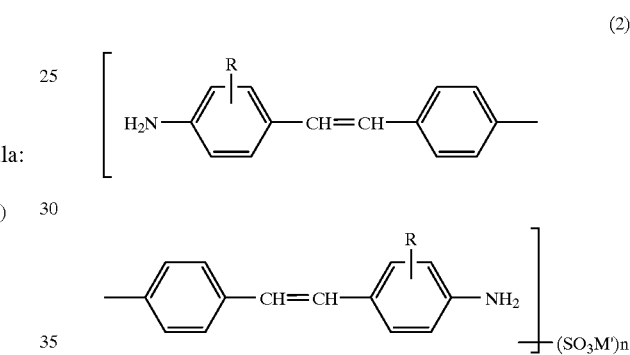

(2)

in which R, M' and n have their previous significance; and

C) reductively de-aminating the compound of formula (2) obtained in step (B) to produce a compound having the formula (1); and converting any optionally substituted phenyl group M' to a group M.

28. A process according to claim 27 in which, in step (C), the compound of formula (2) obtained in step (B) is firstly diazotised to produce a compound having the formula:

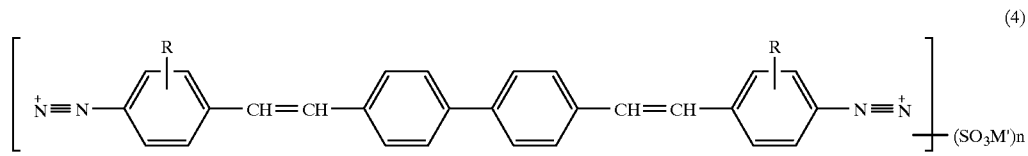

(4)

in which R, M' and n have their previous significance; and then the diazo groups in the compound of formula (4) so obtained are reductively cleaved to obtain a compound of formula (1).

29. A process according to claim 28 in which, in the compounds of formula (4), M' is hydrogen or a salt-forming colourless cation, and the reductive cleavage of the diazo groups is effected in the presence of an alcohol or dimethylformamide, as solvent, and in the presence of copper, iron, zinc or UV light, as catalyst.

30. A process according to claim 29 in which the alcohol solvent is a $C_1$–$C_4$ alcohol or benzyl alcohol.

31. A process according to claim 29 in which the reductive cleavage of the diazo groups is effected in the presence of $Cu_2O$/ethanol.

32. A process according to claim 28 in which, in the compounds of formula (4), M' is optionally substituted phenyl, and the reductive cleavage of the diazo groups is effected in the presence of hypophosphorous acid.

\* \* \* \* \*

UNITED STATES PATENT AND TRADEMARK OFFICE
CERTIFICATE OF CORRECTION

PATENT NO. : 5,929,270

DATED : JULY 27, 1999

INVENTOR(S) : DIETMAR HÜGLIN ET AL. AL.

It is certified that error appears in the above-identified patent and that said Letters Patent is hereby corrected as shown below:

On the title page, Section [30] should read:

-- [30]      Foreign Application Priority Data

May 29, 1997      United Kingdom      9710925.0 --.

Signed and Sealed this

Third Day of April, 2001

Attest:

NICHOLAS P. GODICI

*Attesting Officer*      *Acting Director of the United States Patent and Trademark Office*